United States Patent
O'Lenick, Jr. et al.

(10) Patent No.: US 6,498,263 B1
(45) Date of Patent: Dec. 24, 2002

(54) ALKOXYLATED SILICONE CARBOXYLATE—AMIDO CATIONIC COMPLEXES USED IN PERSONAL CARE APPLICATIONS

(75) Inventors: Anthony J. O'Lenick, Jr., Dacula, GA (US); Charles Buffa, Paterson, NJ (US)

(73) Assignee: Biosil Research Institute, Paterson, NJ (US)

( * ) Notice: Subject to any disclaimer, the term of this patent is extended or adjusted under 35 U.S.C. 154(b) by 0 days.

(21) Appl. No.: 10/188,995

(22) Filed: Jul. 5, 2002

(51) Int. Cl.$^7$ .................................................. C07F 7/10
(52) U.S. Cl. .............. 556/419; 424/70.122; 424/70.21; 424/70.28; 554/39; 554/77
(58) Field of Search .................... 556/4, 9; 424/70.122, 424/70.21, 70.28; 554/39, 77

(56) References Cited

U.S. PATENT DOCUMENTS 5,296,625 A    3/1994  O'Lenick
6,313,256 B1 * 11/2001  O'Lenick, Jr. .......... 556/419 X

* cited by examiner

*Primary Examiner*—Paul F. Shaver

(57) ABSTRACT

The present invention relates to a series of novel silicone alkoxylated esters which have terminal carboxyl groups that form salt complexes with certain amid containing cationic compounds to form very mild conditioning products suited for personal care applications like shampoos, body wash, hand wash and bath products.

19 Claims, No Drawings

ALKOXYLATED SILICONE CARBOXYLATE— AMIDO CATIONIC COMPLEXES USED IN PERSONAL CARE APPLICATIONS

BACKGROUND OF THE INVENTION

1. Field of the Invention

The present invention relates to a series of novel silicone alkoxylated esters which have terminal carboxyl groups that form salt complexes with certain amid containing cationic compounds to form very mild conditioning products suited for personal care applications like shampoos, body wash, hand wash and bath products.

2. Description of the Related Art

There has been a long felt need for a shampoo product that provides conditioning and softening properties when applied to the hair, and is at the same time mild to the hair, skin and eyes. This is most important in the area of baby shampoo, where tearing is an additional concern.

The classical way to get conditioning is to incorporate cationic compounds into the shampoo. These products provide acceptable softness and anti-static properties when applied to the hair, and a good after feel when applied to the skin, but are aggressive to the skin and eye, allowing for their use at low levels in general use products, and not at all in baby and sensitive skin products. Included in this group are compounds like stearyl dimethyl benzyl alkonium chloride and cetyl tri-methyl ammonium chloride. There have been few products mild enough to use in sensitive skin products.

U.S. Pat. No. 5,296,625, incorporated herein by reference, issued March 1994 to O'Lenick et al describes a class of carboxy substituted silicone compounds useful as raw materials in the practice of the current invention. It is by proper selection of the compounds of the U.S. Pat. No. 5,296,625 and the cationic amido compound that the products of the present invention are prepared.

U.S. Pat. No. 3,560,544, issued Feb. 2, 1971, to Haulska et al likewise discloses carboxy substituted silicone polymers. These polymers are also useful as raw materials in the preparation of the compounds of the present invention.

THE INVENTION

Object of the Invention

It is the object of the present invention to provide novel silicone fatty amido quat compounds having outstanding conditioning properties at low concentrations and at the same time are very mild to the skin and eye.

These compounds are substantive to the surface of hair and have increased solubility in fatty materials including mineral oil, fatty triglycerides and traditional fatty quaternary ammonium compounds. It needs to be clearly understood that with the introduction of silicone into the molecule and with the formation of a complex (a salt) the resulting conditioning complex has unique properties.

Traditionally, one would think of a conditioner as having a water-loving (hydrophilic) group and a water-hating (hydrophilic)group. We have learned this approach, while simplistic is not accurate. The water-hating (hydrophobic) group is insoluble in water, but can be either a silicone or oil soluble group, or in a preferred case both.

In order to make the compounds of the current invention, we consider the molecule as having a water loving (hydrophilic group) an oil loving (oleophilic group) and silicone loving (siliphilic group) in the molecule. The group opposites then are three, hydrophobic (water hating), oleophobic (oil hating), siliphobic (silicone hating). Consequently, hydrophobic (water hating) materials can be either oleophilic or siliphilic. oleophobic (oil hating) materials may be either hydrophilic or siliphilic. Siliphobic (silicone hating) materials may be either oleophilic or hydrophilic. Only by balancing the product and having a cationic charge on it, can the desired improved conditioning be achieved.

SUMMARY OF THE INVENTION

Objectives of the Invention

The present invention relates to complexes of novel silicone alkoxylated esters, which contain carboxyl groups that are combined with specific arnido quats to form the desired conditioning products.

The present invention is also directed toward a process for conditioning hair, which comprises contacting the hair with and effective conditioning amount of the compounds of the present invention. The effective conditioning concentration ranges from 0.01 to 25% by weight of the compound.

DETAILED DESCRIPTION OF THE INVENTION

The compounds of the present invention therefore have a pendant group, which is as follows:

$$R'-(Si(Me)_2-O-Si(Me)(R)-)_o-(O-Si(Me)(R^1)-)_q-O-Si(Me)_2-R'$$

wherein;

Me is methyl;

R and R' are $CH_3$ or $-(CH_2)_3-O-(EO)_a-(PO)_b-(EO)_c-C(O)-R''-C(O)-O^-$ $$R^2-N^+(R^3)(R^4)-CH_2CH_2CH_2-N(H)-C(O)-R^5$$

with the proviso that both R and R' are not $CH_3$;

R" is selected from the group consisting of $-CH_2-CH_2-$; $-CH=CH-$; $-CH_2-C(R^7)-H$;

[cyclohexenyl and tetrachlorophenyl structures] and ;

$R^1$ is selected from the group consisting of lower alkyl $CH_3(CH)_n-$ and phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

$R^2$, $R^3$ and $R^4$ are all $CH_3$;

$R^5$ is $CH_3-(CH2)_d-$;

d is an integer ranging from 14 to 22;

$R^7$ is alkyl having from 1 to 20 carbon atoms.

The complexes of the present invention are made by making a salt of the carboxy silicone of O'Lenick's U.S. Pat. No. 5,296,625, incorporated herein by reference, as follows;

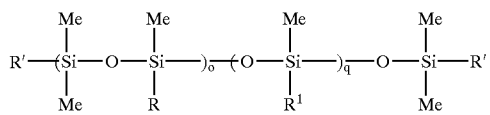

wherein;

Me is methyl;

R and R' are $CH_3$ or $-(CH_2)_3-O-(EO)_a-(PO)_b-(EO)_c-C(O)-R"-C(O)-OH$ with the proviso that both R and R' are not $CH_3$;

R" is selected from the group consisting of $-CH_2-CH_2-$; $-CH=CH-$; $-CH_2-C(R^7)-H$;

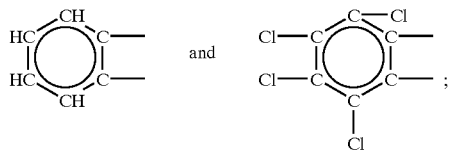

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

$R^7$ is alkyl having from 1 to 20 carbon atoms.

with certain alkyl amido cationic compounds conforming to the following structure:

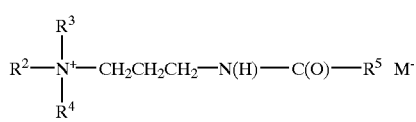

wherein;

$R^2$, $R^3$ and $R^4$ are all $CH_3$;

$R^5$ is $CH_3-(CH_2)_d-$;

M is a anion, needed for charge balance, and is selected from the group consisting of Cl, Br, and $CH_3SO_4$, d is an integer ranging from 14 to 22.

Another aspect of the present invention is a process of treating hair which comprises contacting the hair with an effective conditioning concentration of a compound conforming to the following structure;

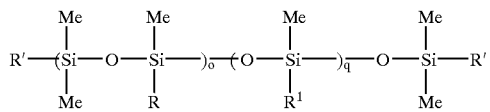

wherein;

Me is methyl;

R and R' are $CH_3$ or $-(CH_2)_3-O-(EO)_a-(PO)_b-(EO)_c-C(O)-R"-C(O)-O^-$

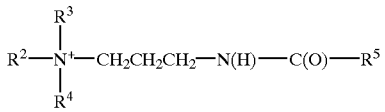

with the proviso that both R and R' are not $CH_3$;

R" is selected from the group consisting of $-CH_2-CH_2-$; $-CH=CH-$; $-CH_2-C(R^7)-H$;

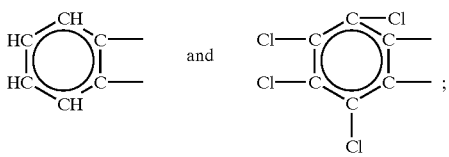

$R^1$ is selected from the group consisting of lower alkyl $CH_3(CH)_n-$ and phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

$R^2$, $R^3$ and $R^4$ are all $CH_3$;

$R^5$ is $CH_3-(CH_2)_d-$;

d is an integer ranging from 14 to 22;

$R^7$ is alkyl having from 1 to 20 carbon atoms.

The effective conditioning concentration ranges from 0.01 to 25% by weight of the compound.

PREFERRED EMBODIMENTS

In a preferred embodiment of the complex n is 14.

In a preferred embodiment of the complex n is 16.

In a preferred embodiment of the complex n is 18.

In a preferred embodiment of the complex n is 20.

In a preferred embodiment of the complex n is 22.

In a preferred embodiment of the complex R" is $-CH_2-CH_2-$.

In a preferred embodiment of the complex R" is $-CH=CH-$.

In a preferred embodiment of the complex R" is

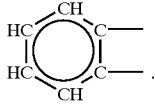

In a preferred embodiment of using the complex n is 14.

In a preferred embodiment of using the complex n is 16.

In a preferred embodiment of using the complex n is 18.

In a preferred embodiment of using the complex n is 20.

In a preferred embodiment of using the complex n is 22.

In a preferred embodiment of using the complex R" is $-CH_2-CH_2-$.

In a preferred embodiment of using the complex R" is $-CH=CH-$.

In a preferred embodiment of using the complex R" is

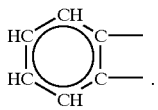

In a preferred embodiment, the effective conditioning concentration ranges from 0.01 to 25% by weight of the compound

EXAMPLES

Carboxy Silicone

The compounds used in the preparation of the complexes of the present invention are taken from U.S. Pat. No. 5,296,625 issued in 1994 to O'Lenick, incorporated herein by reference.

Examples 1–19

| Example | O'Lenick Example |
|---------|------------------|
| 1  | 14 |
| 2  | 15 |
| 3  | 16 |
| 4  | 17 |
| 5  | 18 |
| 6  | 19 |
| 7  | 20 |
| 8  | 21 |
| 9  | 22 |
| 10 | 23 |
| 11 | 24 |
| 12 | 25 |
| 13 | 26 |
| 14 | 27 |
| 15 | 28 |
| 16 | 29 |
| 17 | 30 |
| 18 | 31 |
| 19 | 32 |

Examples 20–29

Amido Cationic Compounds

The amido cationic compounds of the present invention are commercially available from a variety of sources including Siltech Corporation, Toronto Ontario Canada, and Croda Inc, of New Jersey USA.

They conform to the following structure;

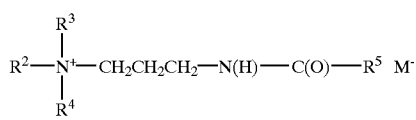

wherein;

$R^2$, $R^3$ and $R^4$ are all $CH_3$;

$R^5$ is $CH_3$—$(CH_2)_d$—;

M is a anion, needed for charge balance, and is selected from the group consisting of Cl, Br, and $CH_3SO_4$;

d is an integer ranging from 14 to 22.

EXAMPLES

| Example Number | $R^5$ n | M |
|---|---|---|
| 20 | 14 | Cl |
| 21 | 16 | Cl |
| 22 | 18 | Cl |
| 23 | 20 | Cl |
| 24 | 22 | Cl |
| 25 | 14 | $CH_3SO_4$ |
| 26 | 16 | Br |
| 27 | 18 | $CH_3SO_4$ |
| 28 | 20 | $CH_3SO_4$ |
| 29 | 22 | Br |

Preparation of Complexes

The complexes of the present invention are made by combining the anionic silicone raw material together with the cationic compound, then neutralizing the resultant mixture with base to pH of 6–7. The resulting complex is a mixed salt of the silicone, the quat and an inorganic salt based upon the nature of "M" used.

| | Carboxy Silicone | | Amido Cationic Compounds | | Water |
|---|---|---|---|---|---|
| Example | Example | Grams | Example | Grams | Grams |
| 30 | 1  | 1,110  | 20 | 378 | 3,720 |
| 31 | 2  | 2,429  | 21 | 406 | 7,088 |
| 32 | 3  | 2,147  | 22 | 434 | 6,452 |
| 33 | 4  | 5,398  | 23 | 462 | 14,650 |
| 34 | 5  | 533    | 24 | 490 | 2,557 |
| 35 | 6  | 4,723  | 25 | 452 | 12,938 |
| 36 | 7  | 3,083  | 26 | 449 | 8,830 |
| 37 | 8  | 3,750  | 27 | 508 | 10,645 |
| 38 | 9  | 1,663  | 28 | 536 | 5,500 |
| 39 | 10 | 1,288  | 29 | 536 | 4,560 |
| 40 | 11 | 6,100  | 29 | 508 | 16,520 |
| 41 | 12 | 10,115 | 28 | 536 | 26,627 |
| 42 | 13 | 50,269 | 27 | 508 | 126,942 |
| 43 | 14 | 86,185 | 26 | 449 | 216,585 |
| 44 | 15 | 2,655  | 25 | 452 | 7,767 |
| 45 | 16 | 2,370  | 24 | 490 | 7,150 |
| 46 | 17 | 5,227  | 23 | 462 | 14,222 |
| 47 | 18 | 500    | 22 | 436 | 2,340 |
| 48 | 19 | 5,723  | 21 | 406 | 15,323 |

Applications

The compounds of the present invention are very substantive to the skin and hair. They are effective in providing conditioning and softening is body washes, shampoos, hand soap, and dish detergents at concentrations of between 0.1 and 2.0% by weight.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A complex conforming to the following structure;

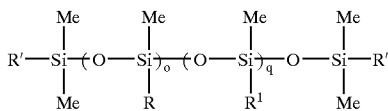

wherein;

Me is methyl;

R and R' are $CH_3$ or —$(CH_2)_3$—O—$(EO)_a$—$(PO)_b$—$(EO)_c$—C(O)—R"—C(O)—O—

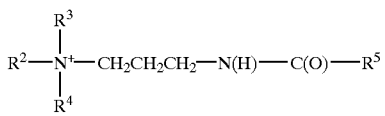

with the proviso that both R and R' are not $CH_3$;

R" is selected from the group consisting of —$CH_2$—$CH_2$—; —CH=CH—; —$CH_2$—$C(R^7)$—H;

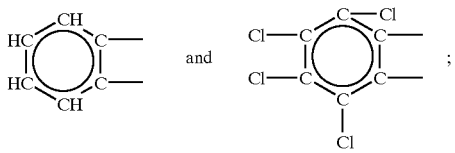

$R^1$ is selected from the group consisting of lower alkyl $CH_3(CH)_n$— and phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;

q is an integer ranging from 0 to 500;

$R^2$, $R^3$ and $R^4$ are all $CH_3$;

$R^5$ is $CH_3$—$(CH_2)_d$—;

d is an integer ranging from 14 to 22;

$R^7$ is alkyl having from 1 to 20 carbon atoms.

2. A complex of claim 1 wherein n is 14.
3. A complex of claim 1 wherein n is 16.
4. A complex of claim 1 wherein n is 18.
5. A complex of claim 1 wherein n is 20.
6. A complex of claim 1 wherein n is 22.
7. A complex of claim 1 wherein R" is —$CH_2$—$CH_2$—.
8. A complex of claim 1 wherein R" is —CH=CH—.
9. A complex of claim 1 wherein R" is

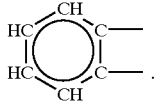

10. A process of treating hair which comprises contacting the hair with an effective conditioning concentration of a compound conforming to the following structure;

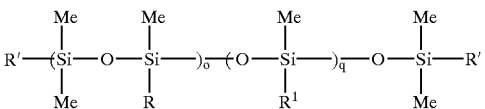

wherein;

Me is methyl;

R and R' are $CH_3$ or —$(CH_2)_3$—O—$(EO)_a$—$(PO)_b$—$(EO)_c$—C(O)—R"—C(O)—O—

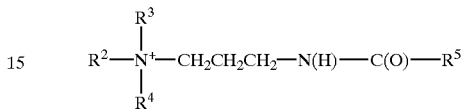

with the proviso that both R and R' are not $CH_3$;

R" is selected from the group consisting of —$CH_2$—$CH_2$—; —CH=CH—; —$CH_2$—$C(R^7)$—H;

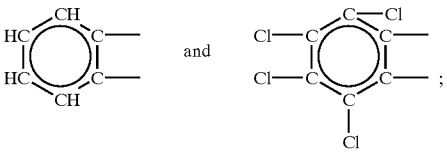

$R^1$ is selected from the group consisting of lower alkyl $CH_3(CH)_n$— and phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;

q is an integer ranging from 0 to 500;

$R^2$, $R^3$ and $R^4$ are all $CH_3$;

$R^5$ is $CH_3$—$(CH_2)_d$—;

d is an integer ranging from 14 to 22;

$R^7$ is alkyl having from 1 to 20 carbon atoms.

11. A process of claim 10 wherein the effective conditioning concentration ranges from 0.01 to 25% by weight of the compound.

12. A process of claim 11 wherein n is 14.
13. A process of claim 11 wherein n is 16.
14. A process of claim 11 wherein n is 18.
15. A process of claim 11 wherein n is 20.
16. A process of claim 11 wherein n is 22.
17. A process of claim 11 wherein R" is —$CH_2$—$CH_2$—.
18. A process of claim 11 wherein R" is —CH=H—.
19. A process of claim 11 wherein R" is

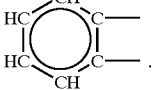

* * * * *